US00PP18748P2

(12) United States Plant Patent
Smith

(10) Patent No.: US PP18,748 P2
(45) Date of Patent: Apr. 22, 2008

(54) ***ASTER* PLANT NAMED 'YOSLOOPY'**

(50) Latin Name: *Aster hybrida*
Varietal Denomination: Yosloopy

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/472,747

(22) Filed: Jun. 22, 2006

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Aster* plant named 'Yosloopy', characterized by its uniform, outwardly spreading and mounded plant habit; freely branching growth habit; dark green-colored foliage; uniform flowering habit; natural flowering season early September in the Northern Hemisphere; daisy-type inflorescence with light violet blue-colored ray florets; and good garden performance.

1 Drawing Sheet

Botanical designation: *Aster hybrida.*
Cultivar denomination: 'Yosloopy'.

BACKGROUND OF THE INVENTION

The present invention relates to a new and distinct cultivar of *Aster* plant, botanically known as *Aster hybrida* and hereinafter referred to by the name 'Yosloopy'.

The objective of the breeding program is to create new potted *Aster* cultivars with uniform plant growth habit, good vigor and strong branching habit, numerous inflorescences, desirable and unique floret colors, uniform flowering response and good garden performance.

The new *Aster* originated from an open-pollination in February, 2002, in Alva, Fla. of the *Aster hybrida* cultivar White Swan, not patented, as the female, or seed, parent with an unknown *Aster hybrida* seedling selection, as the male, or pollen, parent. The new *Aster* was discovered and selected by the Inventor as a single flowering plant within the progeny of the stated open-pollination in a controlled environment Alva, Fla. during the fall of 2002. The selection of this plant was based on its uniform plant growth habit, vigor, desirable floret color and postproduction longevity.

Asexual reproductive of the new *Aster* by vegetative tip cuttings was first conducted in Alva, Fla. in January, 2003. Asexual reproduction by cuttings has shown that the unique features of this new *Aster* are stable and reproduced true to type in successive generations.

SUMMARY OF THE INVENTION

Plants of the cultivar Yosloopy have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yosloopy'. These characteristics in combination distinguish 'Yosloopy' as a new and distinct potted *Aster* cultivar:

1. Uniform, outwardly spreading and mounded plant habit.
2. Freely branching growth habit.
3. Dark green-colored foliage.
4. Uniform flowering habit.
5. Natural flowering season early September in the Northern Hemisphere.
6. Daisy-type inflorescences with light violet blue-colored ray florets.
7. Good garden performance.

Plants of the new *Aster* differ from plants of the female parent, the cultivar White Swan, in the following characteristics:

1. Plants of the new *Aster* are more mounding and rounded than plants of the cultivar White Swan.
2. Plants of the new *Aster* flower about five days later than plants of the cultivar White Swan.
3. Plants of the new *Aster* and the cultivar White Swan differ in ray floret color as plants of the cultivar White Swan have white-colored ray florets.

Plants of the new *Aster* can be compared to plants of the *Aster* cultivar Yoballad, disclosed in U.S. Plant Pat. No. 16,318. In side-by-side comparisons conducted in Alva, Fla., plants of the new *Aster* differed from plants of the cultivar Yoballad in the following characteristics:

1. Plants of the new *Aster* were more mounding and rounded than plants of the cultivar Yoballad.
2. Plants of the new *Aster* flowered slightly later than plants of the cultivar Yoballad.
3. Plants of the new *Aster* and the cultivar Yoballad differed in ray floret coloration.
4. Ray florets of plants of the new *Aster* resisted fading better than ray florets of plants of the cultivar Yoballad.

Plants of the new *Aster* can be compared to plants of the *Aster* cultivar Odin Viking, disclosed in U.S. Plant Pat. No. 10,360. In side-by-side comparisons conducted in Alva, Fla., plants of the new *Aster* differed from plants of the cultivar Odin Viking in the following characteristics:

1. Plants of the new *Aster* were smaller and more rounded than plants of the cultivar Odin Viking.
2. Plants of the new *Aster* flowered earlier than plants of the cultivar Odin Viking when grown under natural season conditions.
3. Plants of the new *Aster* and the cultivar Odin Viking differed in ray floret coloration.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster*.

The photograph at the bottom of the sheet comprises a side perspective view of three typical flowering plants of 'Yosloopy' grown in a container.

The photograph at the top of the sheet is a close-up view of typical inflorescences of 'Yosloopy'.

DETAILED BOTANICAL DESCRIPTION

The aforementioned photographs and following observations and measurements describe plants grown during the spring the spring and early summer in Alva, Fla. in a polycarbonate-covered greenhouse and under conditions and practices which approximate those generally used in commercial potted *Aster* production. During the production of the plants, day temperatures averaged 29° C. and night temperatures averaged 21° C. Three unrooted cuttings were directly stuck in 15-containers, exposed to long day/short night conditions, and pinched about three weeks later. About two weeks after the pinch, the photoinductive short day/long night treatments were started. Plants used in the photographs and for the description were about ten to twelve weeks old. In the following description, color references are made to The Royal Horticultural Society Colour Chart, 1995 Edition, except where general terms of ordinary dictionary significance are used.

Botanical classification: *Aster hybrida* cultivar Yosloopy.

Parentage:

*Female, or seed, parent.*—*Aster hybrida* cultivar White Swan, not patented.

*Male, or pollen, parent.*—Unknown *Aster hybrida* seedling selection, not patented.

Propagation:

*Type.*—Terminal vegetative cuttings.

*Time to initiate roots.*—About ten days at temperatures of about 22° C.

*Time to produce a rooted young plant.*—About 16 to 18 days at temperatures of about 22° C.

*Root description.*—Fine, fibrous; white in color.

*Rooting habit.*—Freely branching.

Plant description:

*Appearance.*—Herbaceous daisy-type potted *Aster;* upright with lateral branches outwardly spreading; inverted triangle with uniformly mounded crown. Strong and freely branching growth habit with lateral branches potentially developing at every node; dense and full plants. Vigorous plant growth habit.

*Plant height.*—About 28 cm.

*Plant width, single plant.*—About 22 cm.

*Lateral branches.*—Length: About 25 cm. Diameter: About 3 mm. Internode length: About 9 mm. Strength: Strong. Texture: Smooth, glabrous. Color: 146B.

Foliage description:

*Arrangement.*—Alternate, simple; sessile.

*Length.*—About 3.8 cm.

*Width.*—About 7 mm.

*Shape.*—Narrowly elliptic to lanceolate.

*Apex.*—Acute.

*Base.*—Attenuate.

*Margin.*—Entire.

*Texture, upper and lower surfaces.*—Smooth, glabrous.

*Colors.*—Developing foliage, upper surface: 137A. Developing foliage, lower surface: 137B. Fully expanded foliage, upper surface: 137A; venation, 137A. Fully expanded foliage, lower surface: 137C; venation, 137C.

Inflorescence description:

*Appearance.*—Daisy-type inflorescence form with ligulate-shaped ray florets. Inflorescences borne on terminals above foliage. Disk and ray florets arranged acropetally on a capitulum. Inflorescences not fragrant.

*Flowering response.*—Under natural conditions, plants flower in early September in the Northern Hemisphere. Plants flower within about 35 days when inflorescence initiation and development is induced artificially under short day/long night conditions (at least 13.5 hours of darkness). Inflorescences persistent.

*Quantity of inflorescences.*—Freely flowering habit, about six open inflorescences per lateral stem.

*Inflorescence bud.*—Height: About 7 mm. Diameter: About 6 mm. Shape: Ovoid. Color: 92C.

*Inflorescence size.*—Diameter: About 2.8 cm. Depth (height): About 1.4 cm. Diameter of disc: About 9 mm. Receptacle diameter: About 1 cm. Receptacle height: About 7 mm.

*Ray florets.*—Shape: Ligulate. Orientation: Initially upright, then about 90° from vertical or perpendicular to peduncle; apices reflexing. Length: About 1.8 cm. Width: About 2 mm. Apex: Broadly acute to nearly rounded. Base: Acute. Margin: Entire. Texture, upper and lower surfaces: Smooth, glabrous, satiny. Number of ray florets per inflorescence: About 96 arranged in about three whorls. Color: When opening, upper surface: Close to 92B. When opening, lower surface: Close to 92C. Fully opened, upper surface: Close to 92C. Fully opened, lower surface: Close to 92D.

*Disc florets.*—Arrangement: Massed at center of receptacle. Shape: Tubular, elongated. Apex: Five-pointed. Length: About 1.2 cm. Width, apex: About 2 mm. Width, base: Less than 1 mm. Number of disc florets per inflorescence: About 58. Color: Immature: 146C. Mature: Apex and mid-section: 145D. Base: 157D.

*Phyllaries.*—Number of phyllaries per inflorescence: About 38. Length: About 8 mm. Width: About 1.5 mm. Shape: Lanceolate. Apex: Acute. Base: Truncate. Texture, upper and lower surfaces: Smooth, glabrous. Color, upper and lower surfaces: 147A.

*Peduncles.*—Length, terminal peduncle; About 1.5 cm. Diameter: About 1 mm. Angle: Erect to curving upright. Strength: Strong, flexible. Texture: Smooth, glabrous. Color: 143A.

*Reproductive organs.*—Androecium: Present on disc florets only. Anther shape: Oblong. Anther length: Less than 1 mm. Anther color: 12B. Pollen amount: Scarce. Pollen color: 12B. Gynoecium: Present on both ray and disc florets. Pistil length: About 7 mm. Stigma shape: Bi-parted. Stigma color: 145B. Style length: About 4 mm. Style color: 145C. Ovary color: 157A.

*Seed/fruit.*—Seed and fruit production has not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures form 0° C. to about 38° C.

It is claimed:

1. A new and distinct *Aster* plant named 'Yosloopy' as illustrated and described.

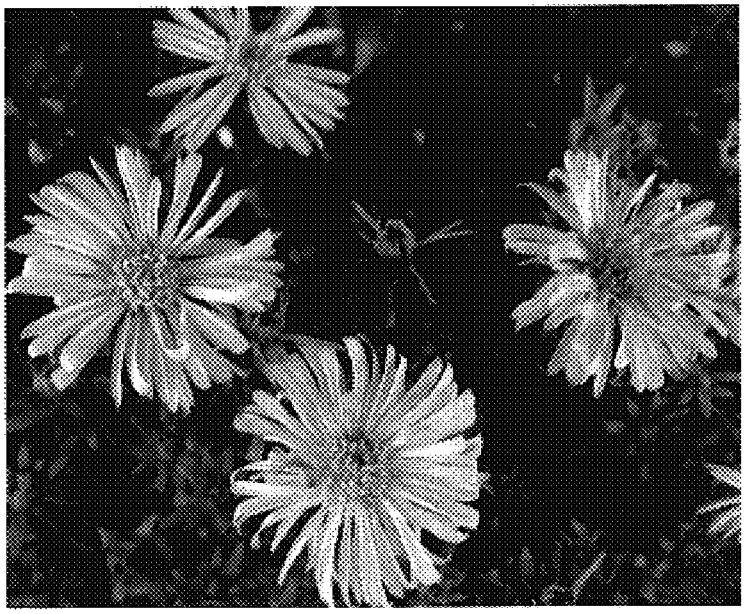
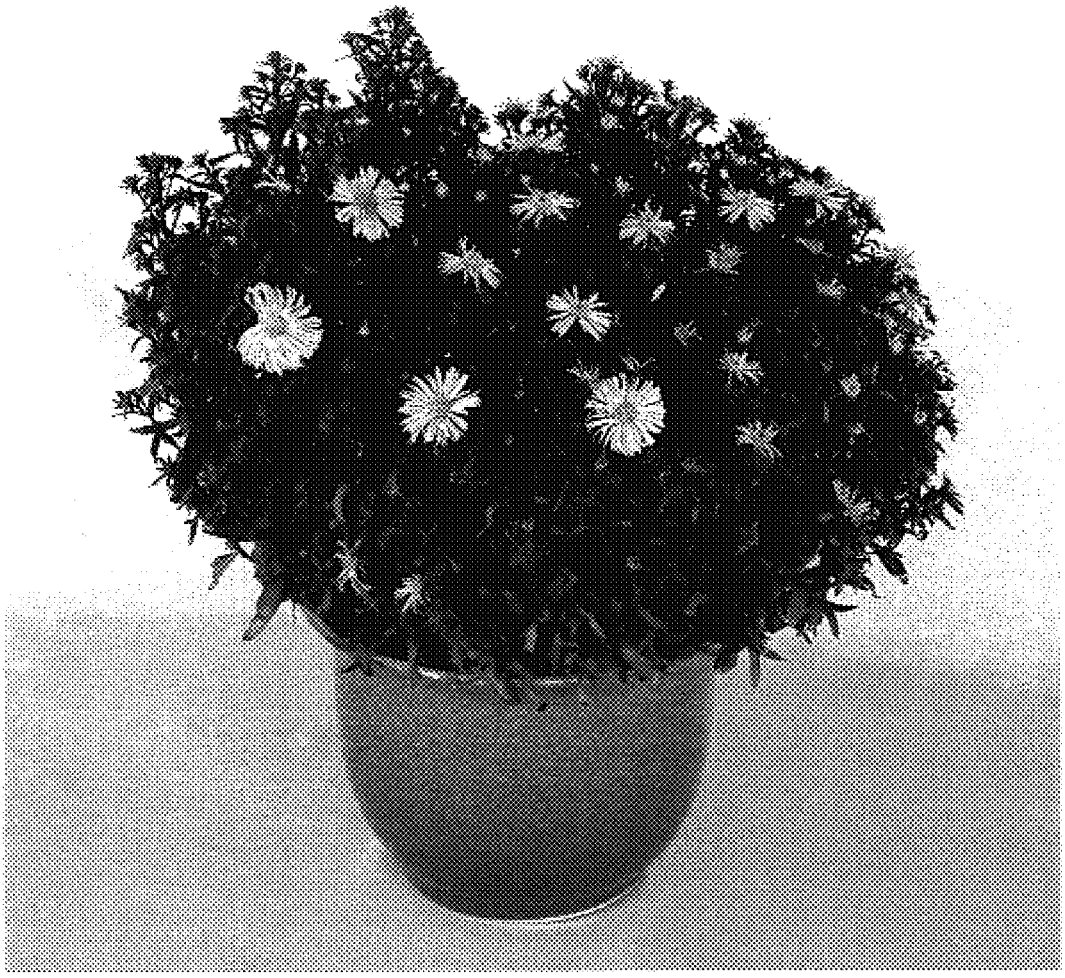

* * * * *